United States Patent
Nambu et al.

(10) Patent No.: US 9,921,171 B2
(45) Date of Patent: Mar. 20, 2018

(54) X-RAY COMPUTER-TOMOGRAPHY APPARATUS

(71) Applicant: Toshiba Medical Systems Corporation, Otawara-shi (JP)

(72) Inventors: Shuya Nambu, Nasushiobara (JP); Takayuki Yamazaki, Nasushiobara (JP); Keiji Matsuda, Nasushiobara (JP); Machiko Iso, Otawara (JP); Atsushi Hashimoto, Otawara (JP); Akira Nishijima, Nasushiobara (JP); Takashi Kanemaru, Yaita (JP); Koichi Miyama, Nasushiobara (JP); Takaya Umehara, Kuki (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 413 days.

(21) Appl. No.: 14/615,640

(22) Filed: Feb. 6, 2015

(65) Prior Publication Data

US 2015/0226861 A1 Aug. 13, 2015

(30) Foreign Application Priority Data

Feb. 10, 2014 (JP) .................................. 2014-023613

(51) Int. Cl.
 *G01N 23/00* (2006.01)
 *G01T 1/24* (2006.01)
 (Continued)

(52) U.S. Cl.
 CPC ......... *G01N 23/046* (2013.01); *G01T 1/2985* (2013.01)

(58) Field of Classification Search
 CPC .... G01N 23/046; G01T 1/2985; A61B 6/032; A61B 6/027; A61B 6/037; A61B 6/4233;
 (Continued)

(56) References Cited

U.S. PATENT DOCUMENTS

| | | | | |
|---|---|---|---|---|
| 6,215,843 | B1 * | 4/2001 | Saito .................... | G01N 23/046 250/370.09 |
| 6,243,438 | B1 * | 6/2001 | Nahaliel ................ | A61B 6/032 378/19 |

(Continued)

FOREIGN PATENT DOCUMENTS

| | | |
|---|---|---|
| JP | 61-29340 | 2/1986 |
| JP | 2000-60836 | 2/2000 |

(Continued)

OTHER PUBLICATIONS

Japanese Office Action dated Nov. 14, 2017 in Japanese Application No. 2014-023613 (2 pages).

*Primary Examiner* — Irakli Kiknadze
(74) *Attorney, Agent, or Firm* — Oblon, McClelland, Maier & Neustadt, L.L.P.

(57) ABSTRACT

An X-ray computer-tomography (CT) apparatus includes an X-ray detector, a reading unit, and a read control unit. The X-ray detector has a first region and a second region at least a part of which is aligned with the first region along a channel direction, the first region in which a plurality of first detection devices that detect X-rays are arranged, the second region in which a plurality of second detection devices having a width smaller in a slice direction than that of the first detection device are arranged. The reading unit reads a signal of the X-rays detected. The read control unit adjusts timing of reading signals from the first detection device and the second detection device according to difference between the size of the first and the second detection device in such a manner that time difference in the reading signals in the slice direction decreases.

8 Claims, 10 Drawing Sheets

(51) Int. Cl.
*G01N 23/04* (2018.01)
*G01T 1/29* (2006.01)

(58) Field of Classification Search
CPC ......... A61B 6/4085; A61B 6/482; A61B 6/14;
A61B 6/5205; A61B 6/542; A61B 6/583;
A61B 6/03; A61B 6/06; A61B 6/4014;
A61B 6/4441; A61B 6/5217; A61B 6/12;
A61B 6/4028; A61B 6/4291; A61B
6/488; A61B 6/5282; A61B 6/481; A61B
6/5258; A61B 6/4021; A61B 6/585
USPC ............. 378/4, 19, 62, 91, 98.8; 250/370.09
See application file for complete search history.

(56) References Cited

U.S. PATENT DOCUMENTS

| | | | |
|---|---|---|---|
| 6,535,571 B2 * | 3/2003 | Von Der Haar | A61B 6/032 250/370.09 |
| 6,658,082 B2 * | 12/2003 | Okumura | A61B 6/032 250/370.09 |
| 6,792,068 B1 * | 9/2004 | Flohr | A61B 6/032 378/19 |
| 7,193,217 B2 * | 3/2007 | Heismann | G01T 1/2928 250/370.09 |
| 7,260,174 B2 * | 8/2007 | Hoffman | A61B 6/032 250/363.09 |
| 7,522,695 B2 * | 4/2009 | Nishide | A61B 6/032 250/370.09 |
| 8,718,227 B2 * | 5/2014 | Dafni | A61B 6/032 378/19 |
| 9,116,248 B2 * | 8/2015 | Abenaim | A61B 6/032 |
| 9,707,411 B2 * | 7/2017 | Beekman | A61N 5/1043 |
| 2001/0005409 A1 * | 6/2001 | Gohno | A61B 6/032 378/19 |
| 2002/0176530 A1 * | 11/2002 | Okumura | A61B 6/032 378/19 |

FOREIGN PATENT DOCUMENTS

| | | |
|---|---|---|
| JP | 2001-174565 | 6/2001 |
| JP | 2005-114367 | 4/2005 |
| JP | 2005-349187 | 12/2005 |
| JP | 2012-157742 | 8/2012 |
| JP | 2012-200555 | 10/2012 |

* cited by examiner

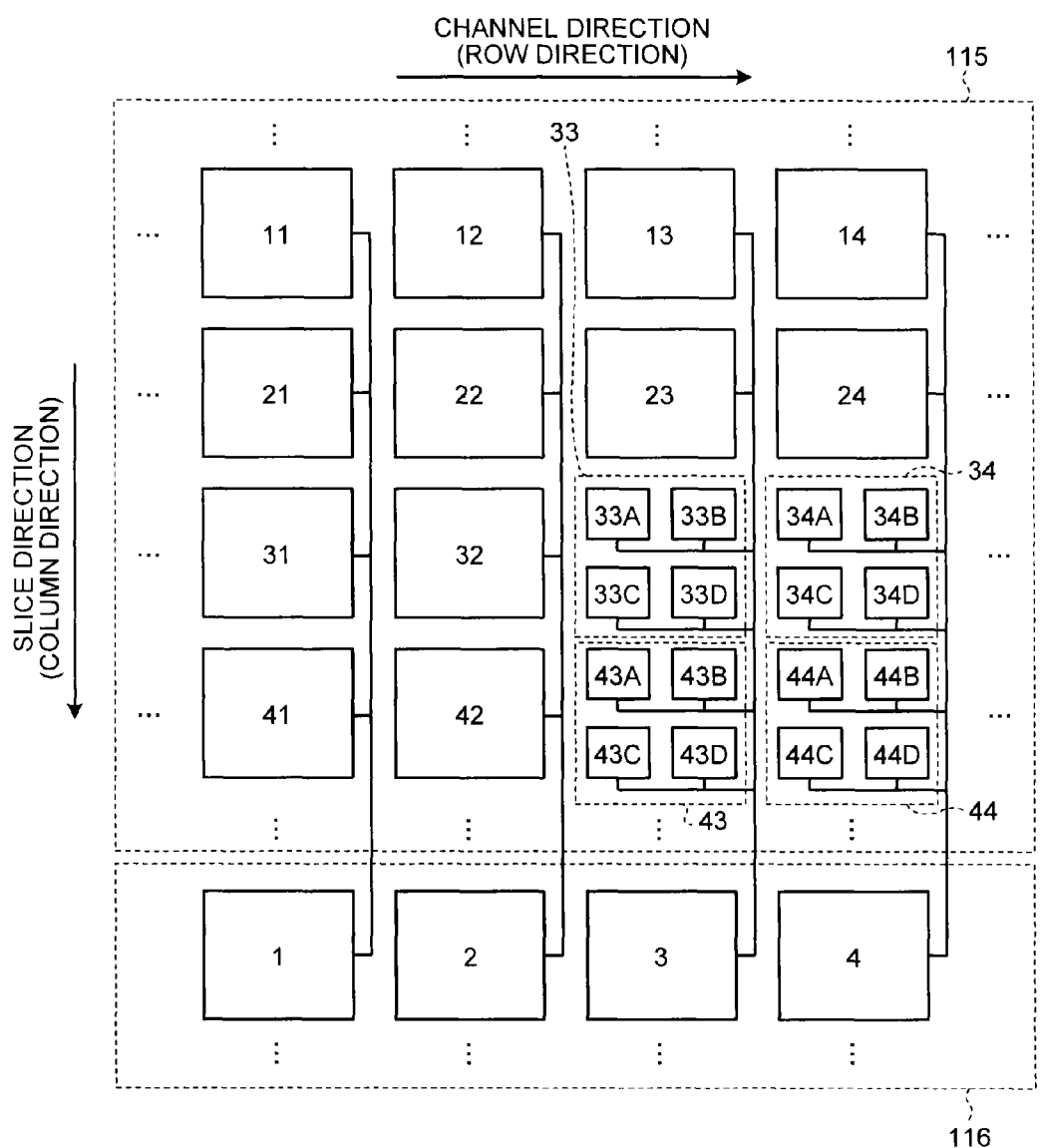

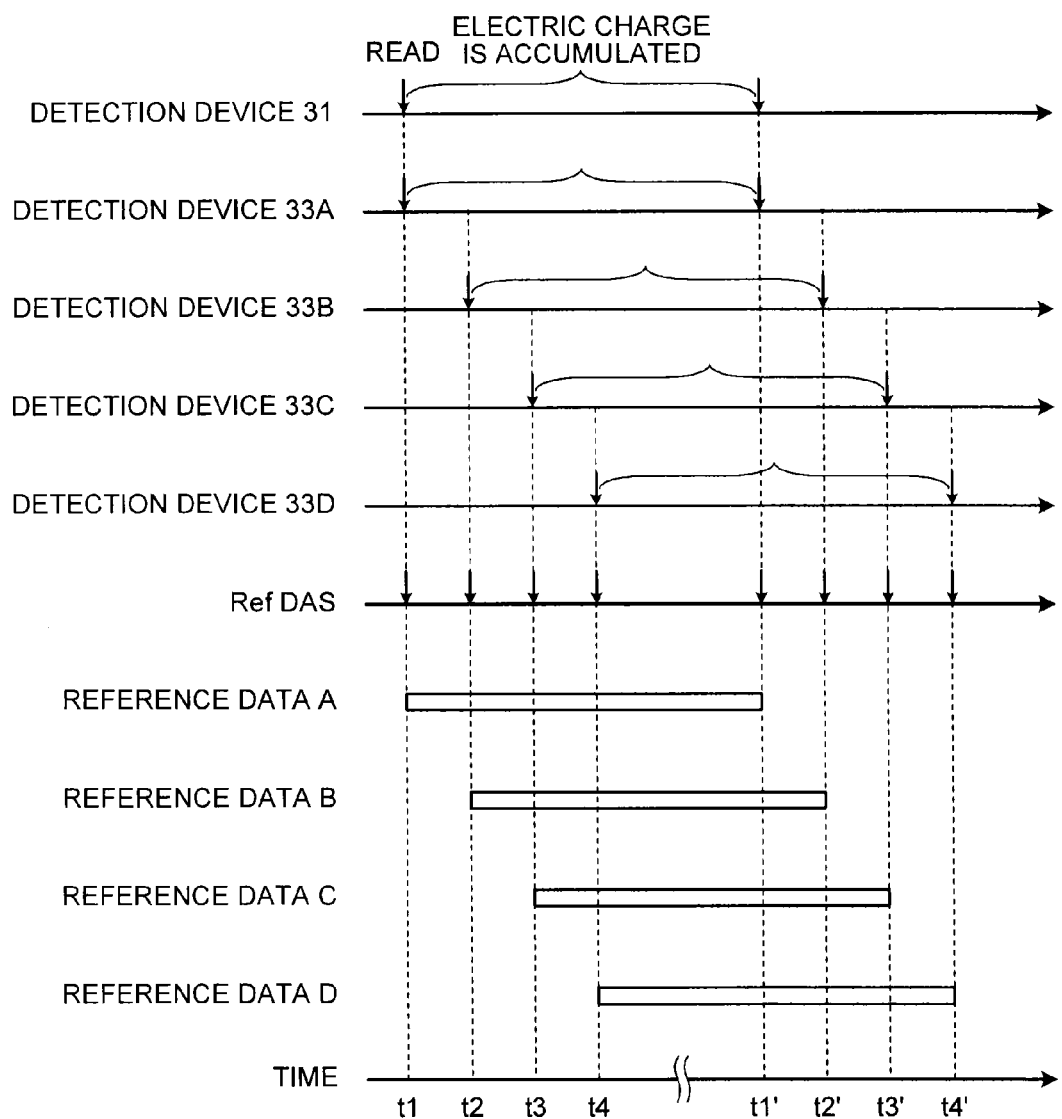

US 9,921,171 B2

X-RAY COMPUTER-TOMOGRAPHY APPARATUS

CROSS-REFERENCE TO RELATED APPLICATIONS

This application is based upon and claims the benefit of priority from Japanese Patent Application No. 2014-23613, filed on Feb. 10, 2014, the entire contents of all of which are incorporated herein by reference.

FIELD

Embodiments disclosed herein relate generally to an X-ray computer-tomography (CT) apparatus.

BACKGROUND

An X-ray CT apparatus is an apparatus that scans a subject using X-rays, and processes thus collected data by a computer, to image internal parts of the subject.

Specifically, the X-ray CT apparatus applies X-rays from various directions to a subject several times, and detects X-ray signals that have passed through the subject with an X-ray detector. This X-ray detector is a multi-row detector that has multiple X-ray detection devices in a channel direction (rotation direction) and a slice direction (body axis direction). The X-ray CT apparatus collect detected signals, and performs preprocessing and the like after analog/digital (A/D) conversion, to generate projection data. The X-ray CT apparatus then performs reconstruction processing based on the projection data, to generate images.

BRIEF DESCRIPTION OF THE DRAWINGS

FIG. 3 is a diagram for explaining a configuration of an X-ray detector and a data collecting circuit according to the first embodiment;

FIG. 11 is a diagram for explaining generation of reference data according to the fourth embodiment.

DETAILED DESCRIPTION

An X-ray CT apparatus of an embodiment includes an X-ray tube, an X-ray detector, a reading unit, and a read control unit. The X-ray tube rotates about a body axis of a subject, and that generates X-rays. The X-ray detector has a first detection region and a second detection region at least a part of which is aligned with the first detection region along a channel direction, the first detection region in which a plurality of first detection devices that detect X-rays passing through the subject are arranged in a slice direction and the channel direction, the second detection region in which a plurality of second detection devices having a width smaller in the slice direction than that of the first detection device are arranged in the slice direction and the channel direction. The reading unit reads a signal of the X-rays that are detected by at least one of the first detection device and the second detection device. The read control unit adjusts timing of reading signals from the first detection device and the second detection device according to difference between the size of the first detection device and the size of the second detection device in such a manner that time difference in read of the signals from the first detection device and the second detection device that are present at positions corresponding to each other in the slice direction decreases.

An X-ray CT apparatus according to an embodiment is explained below with reference to the drawings. Embodiments are not limited to the following embodiments.

First Embodiment

Figure 1:
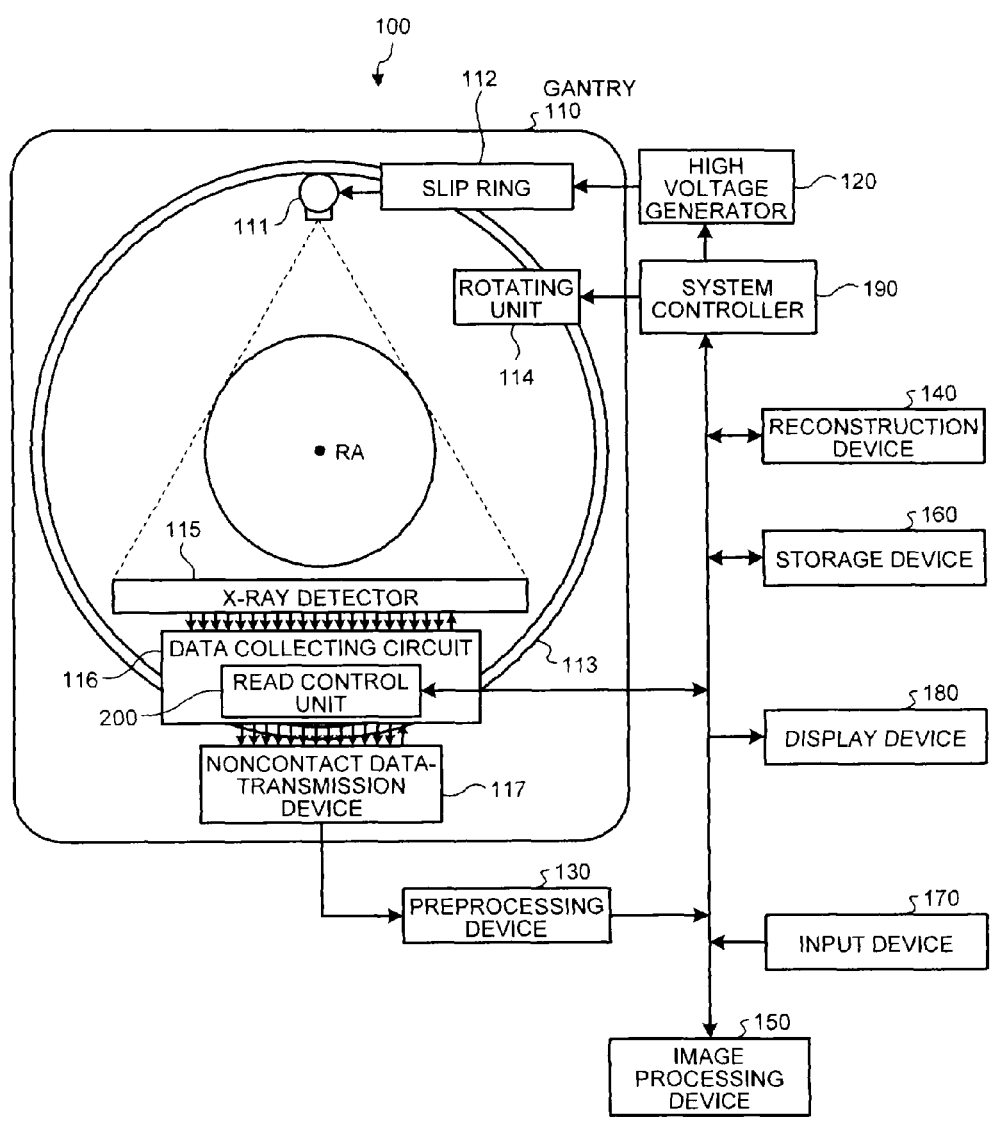
FIG. 1 is a configuration diagram of an X-ray CT apparatus according to a first embodiment.

FIG. 1 is a configuration diagram of an X-ray CT apparatus 100 according to a first embodiment. As indicated in FIG. 1, the X-ray CT apparatus 100 includes a gantry 110, a high voltage generator 120, a preprocessing device 130, a reconstruction device 140, an image processing device 150, a storage device 160, an input device 170, a display device 180, and a system controller 190.

The gantry 110 applies X-rays to a subject, and detects X-rays that have passed through the subject to generate raw data. This gantry 110 includes an X-ray tube 111, a slip ring 112, an X-ray detector 115, a frame 113, a rotating unit 114, a data collecting circuit 116, and a noncontact data-transmission device 117.

The X-ray tube 111 generates X-rays to be applied to the subject by tube voltage and tube current that are supplied by the high voltage generator 120 through the slip ring 112. The X-ray detector 115 detects X-rays that have been generated by the X-ray tube 111 and have passed through the subject. This X-ray detector 115 is explained in detail later.

The frame 113 is formed in a ring shape, and is rotatably arranged about a rotation axis RA. This frame 113 supports the X-ray tube 111 and the X-ray detector 115 so as to be opposed to each other across the rotation axis RA. The rotating unit 114 rotates the frame 113 about the rotation axis RA. For example, the rotating unit 114 rapidly rotates the frame 113 at the speed of 0.4 second/rotation. Thus, the rotating unit 114 rotates the X-ray tube 111 and the X-ray detector 115 about the body axis of a subject.

The X-ray detector 115 is a multi-slice detector that has multiple X-ray detection devices (hereinafter, simply "detection devices") in a channel direction (row direction) and a slice direction (column direction). The channel direction corresponds to a rotation direction of the frame 113, and the slice direction corresponds to a body axis direction of a subject.

Figure 2A:
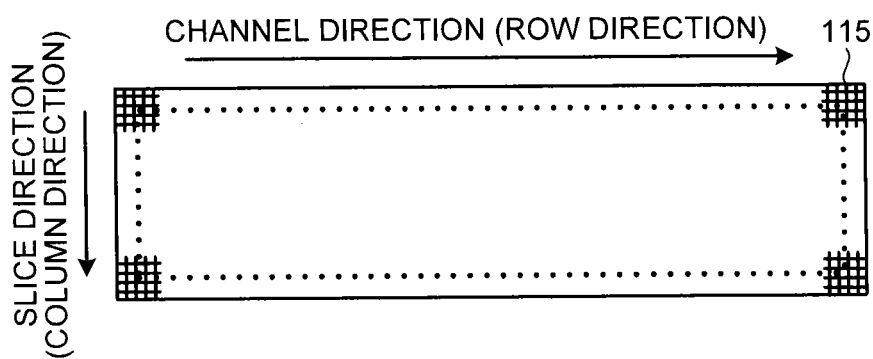
FIGS. 2A and 2B are a diagram for explaining an X-ray detector according to the first embodiment.
Figure 2B:
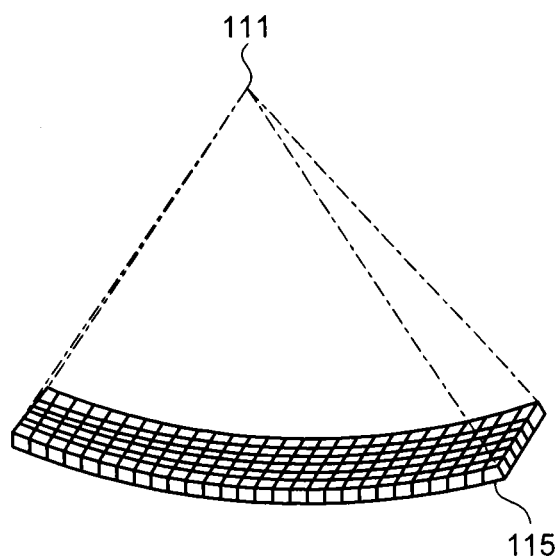

FIGS. 2A and 2B is a diagram for explaining the X-ray detector 115 according to the first embodiment. FIG. 2A is a top plan view indicating a configuration example of the X-ray detector 115. The X-ray detector 115 has detection devices that are arranged, for example, in the channel direction (row direction) and the slice direction (column direction) as indicated in FIG. 2A. FIG. 2B is a perspective view indicating the configuration example of the X-ray detector 115.

For example, in the X-ray detector 115, each detection device detects X-rays that have passed through a subject. In each detection device, electric charge is accumulated according to an amount of detected X-rays. The electric charge accumulated in each detection device is read by the data collecting circuit 116 described later as necessary. In other words, the electric charge accumulated in each detection device is sent to the data collecting circuit 116 as a signal (X-ray transmission signal) of X-rays that have passed through the subject.

The X-ray detector 115 according to the first embodiment has two detection regions (a first detection region and a second detection region) spatial resolutions of which differ (areas of detection devices differ) from each other. In the first detection region is, for example, detection devices having width of X millimeters (mm) (X mm square) are arranged in the channel direction and the slice direction. In the second detection region, for example, two detection devices having width of Y mm (Y mm square) are arranged in each of the channel direction and the slice direction. The X-ray detector 115 according to the first embodiment is also referred to as hybrid detector. Moreover, X and Y are values different from each other.

In other words, the first detection region in which first detection devices that detect X-rays that have passed through a subject are arranged in the slice direction and the channel direction, and the second detection region in which second detection devices having smaller width in the slice direction than the first detection devices are arranged in the slice direction and the channel direction, and at least a part of which is aligned with the first detection region along the channel direction are included.

FIG. 3 is a diagram for explaining a configuration of the X-ray detector 115 and the data collecting circuit 116 according to the first embodiment. In the following, a case in which "Y=X/2" is satisfied is explained. As indicated in FIG. 3, the X-ray detector 115 includes detection devices 11, 12, 13, 14, 21, 22, 23, 24, 31, 32, 41, and 42 having the width of X mm as the first detection region. Moreover, the X-ray detector 115 includes detection devices 33A, 33B, 33C, 33D, 34A, 34B, 34C, 34D, 43A, 43B, 43C, 43D, 44A, 44B, 44C, and 44D having the width of Y mm as the second detection region. In the second detection region, four detection devices that detect X-rays in a range corresponding to the detection device having the width of X mm are also referred to as a detection device group. That is, in a detection device group 33, the detection devices 33A, 33B, 33C, and 33D having the widths of Y mm are arranged in the channel direction and the slice direction. In a detection device group 34, the detection devices 34A, 34B, 34C, and 34D having the width of Y mm are arranged in the channel direction and the slice direction. In a detection device group 43, the detection devices 43A, 43B, 43C, and 43D having the width of Y mm are arranged in the channel direction and the slice direction. In a detection device group 44, the detection devices 44A, 44B, 44C, and 44D having the width of Y mm are arranged in the channel direction and the slice direction. Each of the detection devices is connected to the data collecting circuit 116.

Although a case in which each detection device in the first detection region and each detection group in the second detection region detects X-rays in a range of X mm square is explained herein, embodiments are not limited thereto. For example, a range in which each detection device in the first detection region and each detection group in the second detection region detect X-rays may be changed to an arbitrary length, and further, the lengths in the channel direction and the slice direction are not necessarily required to be the same. Moreover, although a case in which 4 detection devices are allocated in one detection group has been explained, embodiments are not limited thereto. The number of detection devices included in a detection device group may be arbitrarily changed. For example, one detection group may include 16 units of detection devices (4 units in the channel direction and 4 units in the slice direction) having a width of Z (Z=X4) mm. Furthermore, the detection device having the width of X mm is one example of the first detection device. Moreover, the detection device having the width of Y mm is one example of the second detection device.

The data collecting circuit 116 includes more than one data acquisition system (DAS). Each DAS reads (collects) a signal (X-ray transmission signal) of X-rays that are detected by the X-ray detector 115, amplifies, and converts into data (raw data) of a digital signal. The noncontact data-transmission device 117 transmits raw data that is output from each DAS to the preprocessing device 130.

The DAS according to the first embodiment sequentially reads signals of X-rays detected by the detection devices or the detection device groups that are arranged for each channel. That is, relation between the DAS and the detection device is not one-to-one correspondence, and one unit of DAS processes signals detected by more than one detection device. The DAS is one example of a reading unit.

The relation between the DAS and the detection device according to the first embodiment is explained using FIG. 3. As indicated in FIG. 3, for example, the data collecting circuit 116 includes DASs 1, 2, 3, and 4. Out of these, the DAS 1 is connected to the detection devices 11, 21, 31, and 41 that are arranged on the first row in the channel direction. Between the DAS 1 and each of the detection devices 11, 21, 31, and 41, a switch that independently switches connection/disconnection between the DAS and each detection device is arranged. This switch is independently controlled, and the DAS 1 thereby reads signals detected by each of the detection devices 11, 21, 31, and 41 sequentially.

Furthermore, the DAS 2 is connected to the detection devices 12, 22, 32, and 42 that are arranged on the second row in the channel direction. Between the DAS 2 and each of the detection devices 12, 22, 32, and 42, a switch is respectively arranged. This switch is independently controlled, and the DAS 2 thereby reads a signal detected by each of the detection devices 12, 22, 32, and 42 sequentially.

Moreover, the DAS 3 is connected to the detection devices 13, 23, 33A, 33B, 33C, 33D, 43A, 43B, 43C, and 43D that are arranged on the third row in the channel direction. Between the DAS 3 and each of the detection devices 13, 23, 33A, 33B, 33C, 33D, 43A, 43B, 43C, and 43D, a switch is respectively arranged. This switch is independently controlled, and the DAS 3 thereby reads a signal detected by each of the detection devices 13, 23, 33A, 33B, 33C, 33D, 43A, 43B, 43C, and 43D sequentially.

Furthermore, the DAS 4 is connected to the detection devices 14, 24, 34A, 34B, 34C, 34D, 44A, 44B, 44C, and 44D that are arranged on the fourth row in the channel direction. Between the DAS 4 and each of the detection devices 14, 24, 34A, 34B, 34C, 34D, 44A, 44B, 44C, and 44D, a switch is respectively arranged. This switch is independently controlled, and the DAS 4 thereby reads a signal detected by each of the detection devices 14, 24, 34A, 34B, 34C, 34D, 44A, 44B, 44C, and 44D sequentially.

As described, each of the DAS 1, 2, 3, and 4 processes a signal detected by each detection device. The respective DAS 1, 2, 3, and 4 can perform processing in parallel.

In other words, the DASs according to the first embodiment respectively read signals of X-rays detected by at least either one of the first detection device and the second detection device.

Moreover, the data collecting circuit 116 includes a read control unit 200. The read control unit 200 controls timing of reading a signal from each detection device by each DAS. Details of processing performed by the read control unit 200 are described later.

Explanation returns to FIG. 1. The high voltage generator 120 is a device that provides tube voltage and tube current to the X-ray tube 111 of the gantry 110 to generate X-rays. The preprocessing device 130 generates projection data to be a source of image reconstruction by performing correction processing such as sensitivity correction on raw data that is transmitted from the noncontact data-transmission device 117.

The reconstruction device 140 reconstructs image data of a subject by performing predetermined reconstruction processing on the projection data generated by the preprocessing device 130. The image processing device 150 generates a three-dimensional image, a curved multi planner reconstruction (MPR) image, a cross cut image, and the like using the image data that is reconstructed by the reconstruction device 140.

The storage device 160 stores projection data that is generated by the preprocessing device 130, image data that is reconstructed by the reconstruction device 140, various kinds of images that are generated by the image processing device 150, and the like. For example, the storage device 160 is a hard disk drive (HDD), a digital versatile disc (DVD), a drive, or the like.

The input device 170 accepts various kinds of operations made by an operator to the X-ray CT apparatus 100. For example, the input device 170 is a keyboard, a mouse, and the like. The display device 180 outputs various kinds of images that are generated by the reconstruction device 140 or the image processing device 150, a graphic user interface (GUI) to accept various kinds of operations made by an operator, and the like. For example, the display device 180 is a liquid crystal panel, a cathode ray tube (CRT) monitor, or the like.

The system controller 190 controls operation of the entire X-ray CT apparatus 100 based on various kinds of operations accepted by the input device 170. Moreover, the system controller 190 controls read of an X-ray transmission signal that is detected by each detection device by controlling the read control unit 200 described later, based on scan conditions.

When read of signals from the respective detection devices is sequentially performed with such a configuration, time difference can be generated among signals that are collected for each channel.

Figure 4:
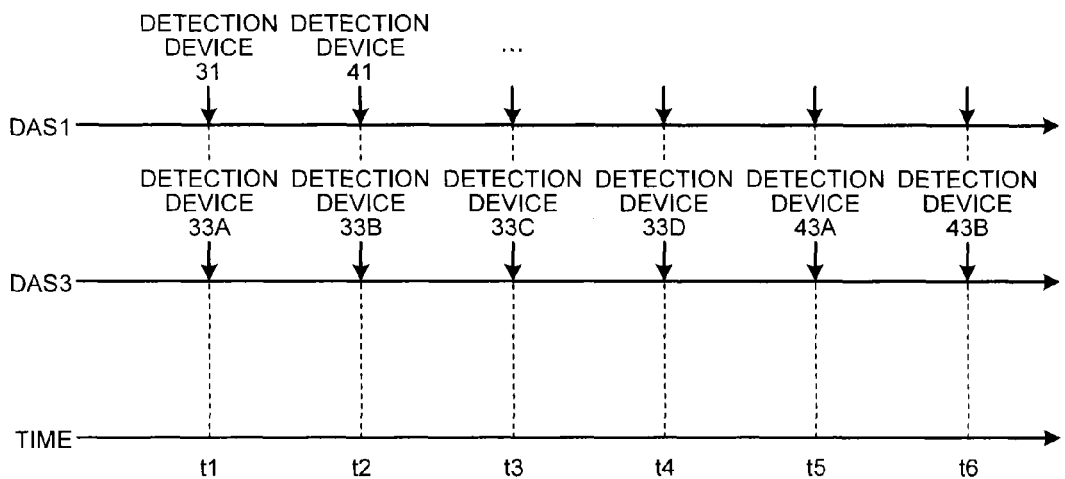
FIG. 4 is a diagram for explaining a problem according to the first embodiment.

FIG. 4 is a diagram for explaining a problem according to the first embodiment. In FIG. 4, a horizontal direction corresponds to time. Furthermore, a downward arrow indicates timing (time) of reading a signal (electric charge) by each DAS. In FIG. 4, a case in which signals up to the second column in the slice direction have been read, and signals from the third column are to be read is explained. Moreover, although timing of reading a signal by the DAS 1 and the DAS 3 exemplified in FIG. 3 is explained herein as one example, the same applies to the other DASs included in the data collecting circuit 116.

As indicated in FIG. 4, for example, when each DAS performs read of signals from each detection device at regular time intervals, time difference is generated in signals collected in different channels even at the same slice position. Specifically, the DAS 1 reads a signal from the detection device 31 at time t1, and reads a signal from the detection device 41 at time t2. Moreover, the DAS 3 reads a signal from the detection device 33A at time t1, and reads a signal from the detection device 33B at time t2, reads a signal from the detection device 33C at time t3. Subsequently, the DAS 3 reads a signal from the detection device 33D at time t4, reads a signal from the detection device 43A at time t5, and reads a signal from the detection device 43B at time t6.

Focusing on timing of reading the detection device 41 and the detection device group 43 on the fourth column in the slice direction, the detection device 41 is read at time t2 while the detection devices 43A and 43B of the detection device group 43 are read at times t5 and t6. This signifies that accumulation time of electric charges accumulated in the detection devices 43A and 43B is longer than electric charges accumulated in the detection device 41. Such difference in the accumulation time increases as the number of detection devices to be read increases. If difference occurs in the accumulation time of electric charges at the same slice position, an error occurs in the amount of electric charges to be read, and as a result, there is a negative effect in the image quality of a generated image.

Therefore, the X-ray CT apparatus 100 according to the first embodiment performs the following processing, thereby improving the image quality of a generated image. In the following, processing performed in the read control unit 200 of the X-ray CT apparatus 100 to achieve this function is explained.

The read control unit 200 according to the first embodiment performs control of synchronizing read of signals from the respective detection devices at the same slice position according to difference between the size of the detection device in the first detection region and the size of the detection device in the second detection region.

In other words, the read control unit 200 performs control of adjusting timing of reading a signal from the first detection device and the second detection device so that time difference in reading signals from the first detection device and the second detection device at corresponding positions in the slice direction decreases, according to difference in the size of the first detection device and the size of the second detection device.

For example, the read control unit 200 performs control of matching timing of reading the detection device having the width of X mm and timing of reading at least one of the detection devices having the width of Y mm in the detection group at the same slice position as the detection device having the width of X mm.

In other words, as adjustment control in reading a detection device group that detects X-rays in a range having the same size as the first detection device, and in which two or more units of the second detection devices are respectively arranged in the slice direction and in the channel direction, the read control unit 200 synchronizes timing of reading the first detection device and timing of reading at least one of the detection devices included in the detection device group at a position corresponding the first detection device in the slice direction.

Specifically, for example, when a detection device having the width of X mm and a detection device group are present at the same slice position, the read control unit 200 performs control of reducing the frequency of reading from the detection device having the width of X mm according to the number of the detection devices having the width of Y mm that are included in the detection device group. Thus, the read control unit 200 synchronizes read from the detection device having the width of X mm and from the detection device having the width of Y mm at the same slice position. The read control unit 200 can determine at which slice position the detection device having the width of X mm and the detection device having the width of Y mm (detection device group) are present, for example, by acquiring information about arrangement pattern of each detection device in the X-ray detector 115 from the system controller 190.

Figure 5:
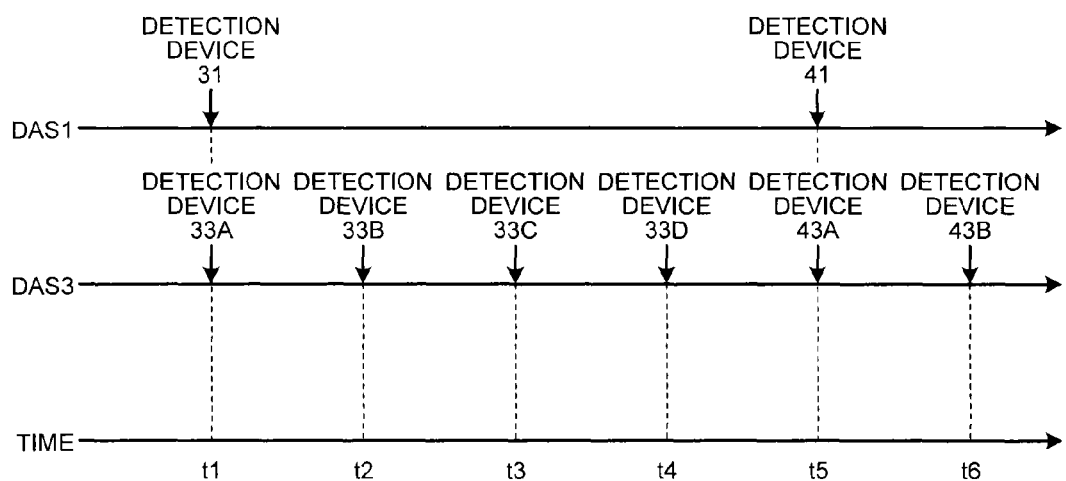
FIG. 5 is a diagram for explaining processing performed by a read control unit according to the first embodiment.

FIG. 5 is a diagram for explaining processing performed by the read control unit 200 according to the first embodiment. In FIG. 5, the horizontal direction corresponds to time. Furthermore, a downward arrow indicates timing of reading a signal by each DAS. In FIG. 5, a case in which signals up to the second column in the slice direction have been read, and signals from the third column are to be read is explained. Moreover, although timing of reading a signal by the DAS 1 and the DAS 3 exemplified in FIG. 3 is explained herein as one example, the same applies to the other DASs included in the data collecting circuit 116.

In an example indicated in FIG. 5, the number of detection devices having the width of Y mm that are included in each detection device group is four. In this case, the read control unit 200 performs control of reducing reading frequency of the DAS 1 such that the DAS 1 performs read once while the DAS 3 performs read four times. Specifically, the read control unit 200 causes the DAS 3 to perform read from the detection devices 33A, 33B, 33C, 33D, 43A, and 43B sequentially at times t1, t2, t3, t4, t5, and t6, respectively. At this time, for the DAS 1, the read control unit 200 cancels read at times t2, t3, t4, and t6. That is, the read control unit 200 causes the DAS 1 to perform read from the detection devices 31 and 41 sequentially at time t1, and t5, respectively. Thus, the read control unit 200 synchronizes, for example, read from the detection device 31 and the detection device group 33 at the third column at times t1 to t4.

As described, the read control unit 200 synchronizes read from the detection device having the width of X mm and from the detection device group at the same slice position.

In other words, when more than one unit of the second detection device included in a detection device group is read by the same reading unit, the read control unit 200 reduces the frequency of reading the first detection device according to the number of the second detection devices included in the detection device group as the adjustment control.

Although a case in which the DAS 3 reads the detection devices in the sequence of 33A, 33B, 33C, and 33D at read of the detection device group 33 has been explained in FIG. 5, it is not limited thereto. For example, the DAS 3 may read the detection devices in the sequence of 33A, 33C, 33B, and 33D, or in another sequence. This read sequence is controlled by sequentially switching the switches between the DAS 3 and the respective detection devices by the read control unit 200. Moreover, the time at which the DAS 1 read the detection device 31 is not limited to time t1, and for example, it may be either one of times t2 to t4. That is, timing of reading the detection device 31 is only required to be synchronized with timing of reading at least one of the detection devices included in the detection device group 33 at the same slice position.

As described above, the X-ray CT apparatus 100 according to the first embodiment includes a hybrid detector that has two detection regions spatial resolutions of which differ from each other. For a detection device having the width of X mm and a detection group that are present at the same slice position, the X-ray CT apparatus 100 performs control of synchronizing read from the detection device and from the detection device having the width of Y mm included in the detection device group. Accordingly, the X-ray CT apparatus 100 suppresses difference in accumulation time of electric charges accumulated in respective detection devices for the detection device having the width of X mm and the detection device group positioned at the same slice position, and therefore enables to improve the image quality of a generated image.

Second Embodiment

Although a case in which detection devices included in a detection device group are read by the same DAS has been explained in the first embodiment, embodiments are not limited thereto. For example, the X-ray CT apparatus 100 can synchronize read also when detection devices included in a detection device group are read by respective different DASs. Therefore, in the second embodiment, processing to synchronize read when the X-ray CT apparatus 100 reads detection devices included in a detection device group by respective different DASs is explained.

The X-ray CT apparatus 100 according to the second embodiment has a configuration similar to that of the X-ray CT apparatus 100 indicated in FIG. 1, but has differences in that each of detection devices included in each detection device group has a DAS, and in a part of processing performed by the read control unit 200. Therefore, in the second embodiment, points that differ from the first embodiment are mainly explained, and explanation of points with functions similar to the configuration that has been explained in the first embodiment is omitted.

A DAS according to the second embodiment is arranged for each detection device included in each detection device group. In other words, for a channel in which the detection device groups are aligned, the same number or more of DASs are arranged as the number of the detection devices included in each of the detection device groups. These DASs are connected to one detection device among the detection devices of each of the detection device groups, and reads a signal from the connected detection device. The DAS may be connected to multiple detection devices and read signals from the connected detection devices sequentially, among different detection device groups.

Figure 6:
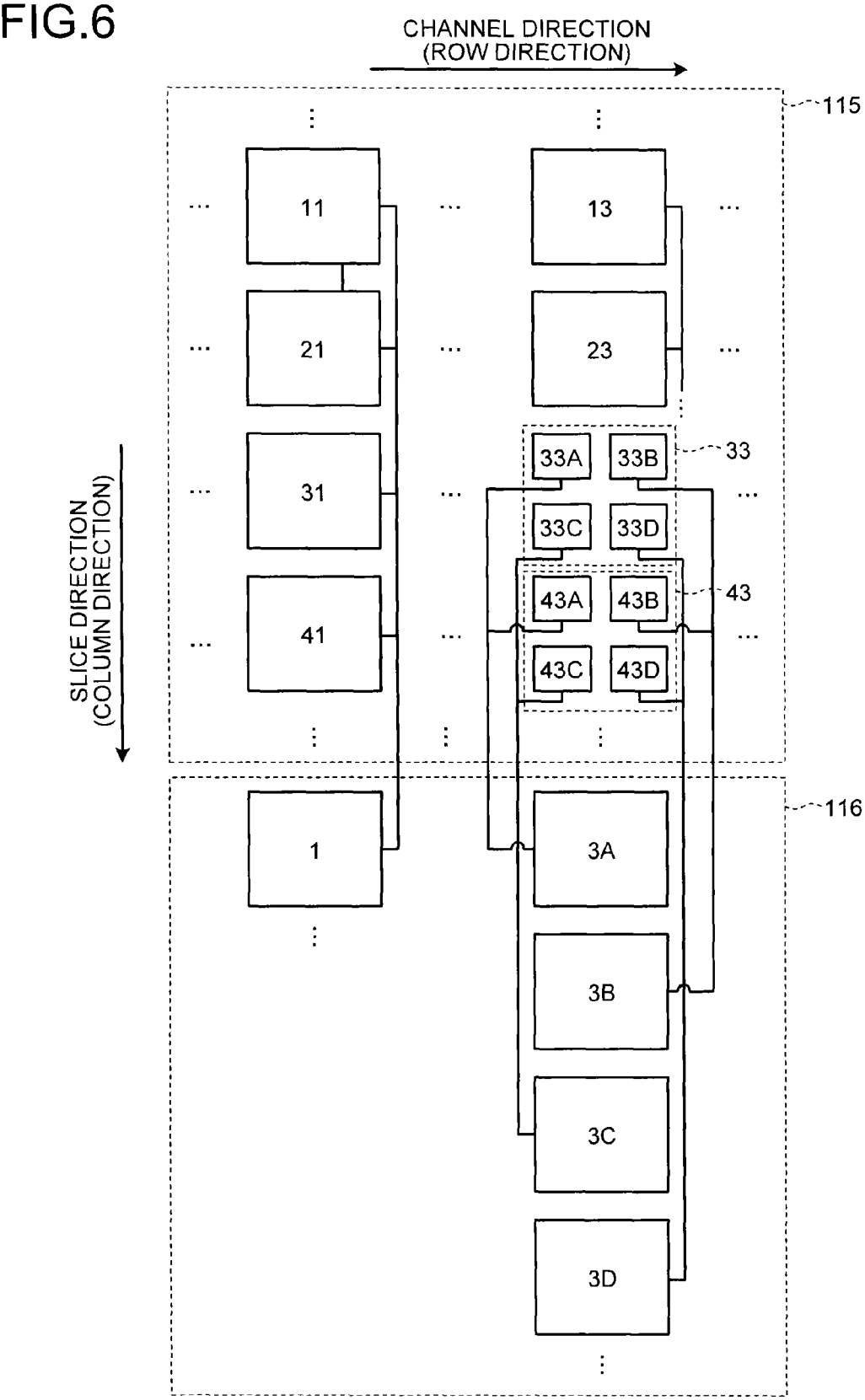
FIG. 6 is a diagram for explaining a configuration of an X-ray detector and a data collecting circuit according to a second embodiment.

FIG. 6 is a diagram for explaining a configuration of the X-ray detector 115 and the data collecting circuit 116 according to the second embodiment. For convenience of explanation, detection devices on the first row and the third row are exemplified among the detection devices exemplified in FIG. 3. The arrangement relation of the DAS 1 and the detection devices 11, 21, 31, and 41 is the same as that in FIG. 3, and therefore, explanation thereof is omitted.

As indicated in FIG. 6, for example, the data collecting circuit 116 includes as many DASs, 3A, 3B, 3C, and 3D, as the number of detection devices included in each of the detection device groups, "four". Among these, the DAS 3A is connected to the detection devices 33A and 43A that are arranged on the third row in the channel direction. Between the DAS 3A and each of the detection devices 33A and 43A, a switch that independently switches connection/disconnection between the DAS and each detection device is arranged. This switch is independently controlled, and the DAS 3A thereby reads signals detected by each of the detection devices 33A and 43A sequentially.

Moreover, the DAS 3B is connected to the detection devices 33B and 43B that are arranged on the third row in the channel direction. Between the DAS 3B and each of the detection devices 33B and 43B, a switch is arranged. This switch is independently controlled, and the DAS 3B thereby reads signals detected by each of the detection devices 33B and 43B sequentially.

Furthermore, the DAS 3C is connected to the detection devices 33C and 43C that are arranged on the third row in the channel direction. Between the DAS 3C and each of the detection devices 33C and 43C, a switch is arranged. This switch is independently controlled, and the DAS 3C thereby reads signals detected by each of the detection devices 33C and 43C sequentially.

Moreover, the DAS 3D is connected to the detection devices 33D and 43D that are arranged on the third row in the channel direction. Between the DAS 3D and each of the detection devices 33D and 43D, a switch is arranged. This switch is independently controlled, and the DAS 3D thereby reads signals detected by each of the detection devices 33D and 43D sequentially.

As described, for a channel in which the detection device groups are arranged, at least as many DASs, 3A, 3B, 3C, and 3D, as the number of detection devices in each of the detection device groups are arranged. Each of the DASs 3A, 3B, 3C, and 3D is connected to one detection device among the detection devices included in each of the detection device groups. The DASs 3A, 3B, 3C, and 3D sequentially read signals from the respective connected detection devices. The DAS 3A, 3B, 3C, and 3D can perform processing in parallel.

The read control unit 200 according to the second embodiment has a function similar to that of the read control unit 200 according to the first embodiment. Furthermore, for a detection device having the width of X mm and a detection device group positioned at the same slice position, the read control unit 200 performs control of synchronizing timing of reading the detection device having the width of X mm and a detection device having the width of Y mm when detection devices having the width of Y mm included in the detection device group are read by respective different DASs.

Figure 7:
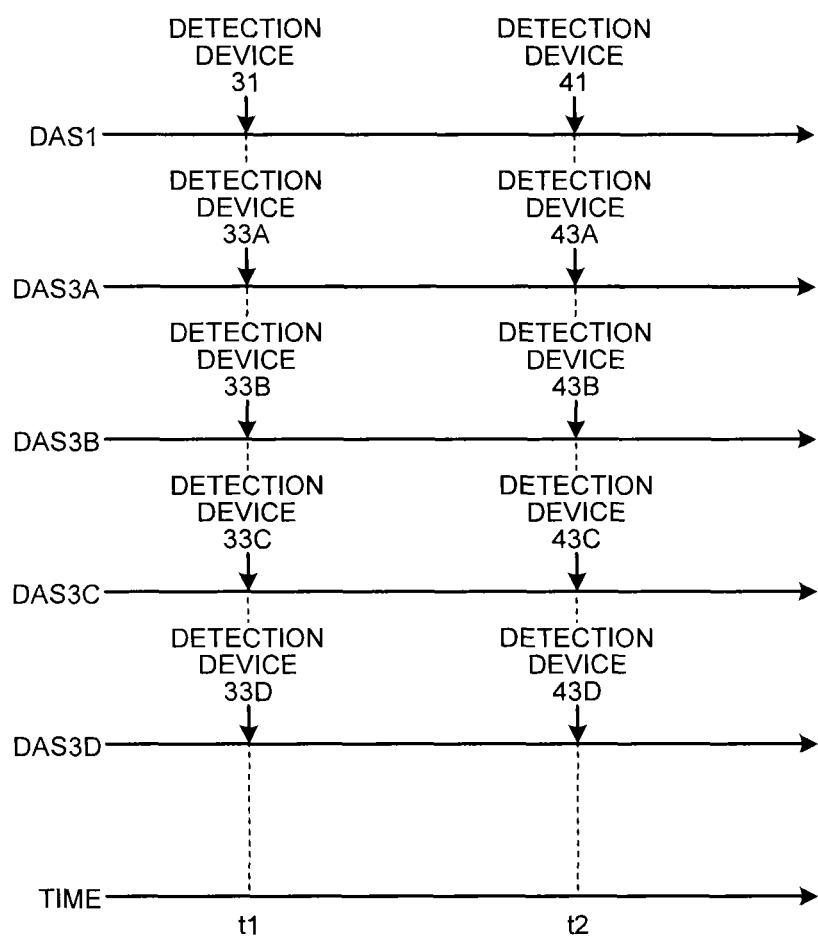
FIG. 7 is a diagram for explaining processing performed by a read control unit according to the second embodiment.

FIG. 7 is a diagram for explaining processing performed by the read control unit 200 according to the second embodiment. In FIG. 7, the horizontal direction corresponds to time. Moreover, a downward arrow indicates timing of reading a signal by each DAS. In FIG. 7, a case in which signals up to the second column in the slice direction have been read, and signals from the third column are to be read is explained. Moreover, although timing of reading a signal by the DAS 1 and the DASs 3A, 3B, 3C, and 3D exemplified in FIG. 6 is explained herein as one example, the same applies to the other DASs included in the data collecting circuit 116.

In the example indicated in FIG. 7, the read control unit 200 synchronizes timing of read by the DASs 1, 3A, 3B, 3C, and 3D. Specifically, at time t1, the read control unit 200 causes the DAS 1 to perform read from the detection device 31, causes the DAS 3A to perform read from the detection device 33A, causes the DAS 3B to perform read from the detection device 33B, causes the DAS 3C to perform read from the detection device 33C, and causes the DAS 3D to perform read from the detection device 33D. Subsequently, at time t2, the read control unit 200 causes the DAS 1 to perform read from the detection device 41, causes the DAS 3A to perform read from the detection device 43A, causes the DAS 3B to perform read from the detection device 43B, causes the DAS 3C to perform read from the detection device 43C, and causes the DAS 3D to perform read from the detection device 43D.

As described, the read control unit 200 synchronizes read from a detection device having the width of X mm and a detection device group that are positioned at the same slice position.

In other words, when the second detection devices included in a detection device group are read by the respective different reading units, the read control unit 200 synchronizes timing of reading the first detection device at a position corresponding to that of the detection device group in the slice direction and of reading each of the second detection devices, as adjustment control.

As described above, the X-ray CT apparatus 100 according to the first embodiment includes a hybrid detector that has two detection regions spatial resolutions of which differ from each other. Furthermore, the X-ray CT apparatus 100 has a DAS for each of detection devices included in each detection device group. For a detection device having the width of X mm and a detection group that are present at the same slice position, the X-ray CT apparatus 100 performs control of synchronizing read from the detection devices having the width of Y mm included in the detection device group and from the detection device having the width of X mm. Accordingly, the X-ray CT apparatus 100 equalizes accumulation time of electric charges accumulated in respective detection devices for the detection device having the width of X mm and the detection device group present at the same slice position, and therefore enables to improve the image quality of a generated image.

Specifically, while read from, for example, the detection device 31 and the detection device group 33 on the third column is synchronized between times t1 to t4 in the first embodiment, the X-ray CT apparatus 100 according to the second embodiment synchronizes at time t1. Therefore, the X-ray CT apparatus 100 according to the second embodiment can further improved the image quality of a generated image.

Third Embodiment

In the second embodiment, a case in which timing of reading a detection device and each of detection devices included in a detection device group present at the same slice position is synchronized by arranging a DAS for each of detection devices included in each detection device group has been explained. However, there is a case in which cross talk occurs in a condition in which detection devices, DASs, and wirings are closely arranged. Cross talk is a phenomenon in which signals passing through adjacent wirings are mixed, or affect each other, and there is a possibility that it leads to deterioration of the image quality of a generate in the X-ray CT apparatus 100. Therefore, in the third embodiment, processing for the X-ray CT apparatus 100 further to suppress occurrence of cross talk is explained.

The X-ray CT apparatus 100 according to the third embodiment has a configuration similar to that (configuration in FIG. 6) of the X-ray CT apparatus 100 explained in the second embodiment, and has a difference in a part of processing performed by the read control unit 200. Therefore, in the third embodiment, points that differ from the second embodiment are mainly explained, and explanation of points with functions similar to the configuration that has been explained in the second embodiment is omitted.

The read control unit 200 according to the third embodiment has a function similar to that of the read control unit 200 according to the first embodiment. Furthermore, for a detection device having the width of X mm and a detection device group present at the same slice position, the read control unit 200 performs control of varying timing of reading respective detection devices having the width of Y mm included in the detection device group.

In other words, to vary timing of reading respective detection devices having the width of Y mm included in a detection device group, the read control unit 200 performs control of reducing reading frequency of each DAS according to the number of the detection devices having the width of Y mm.

Figure 8:
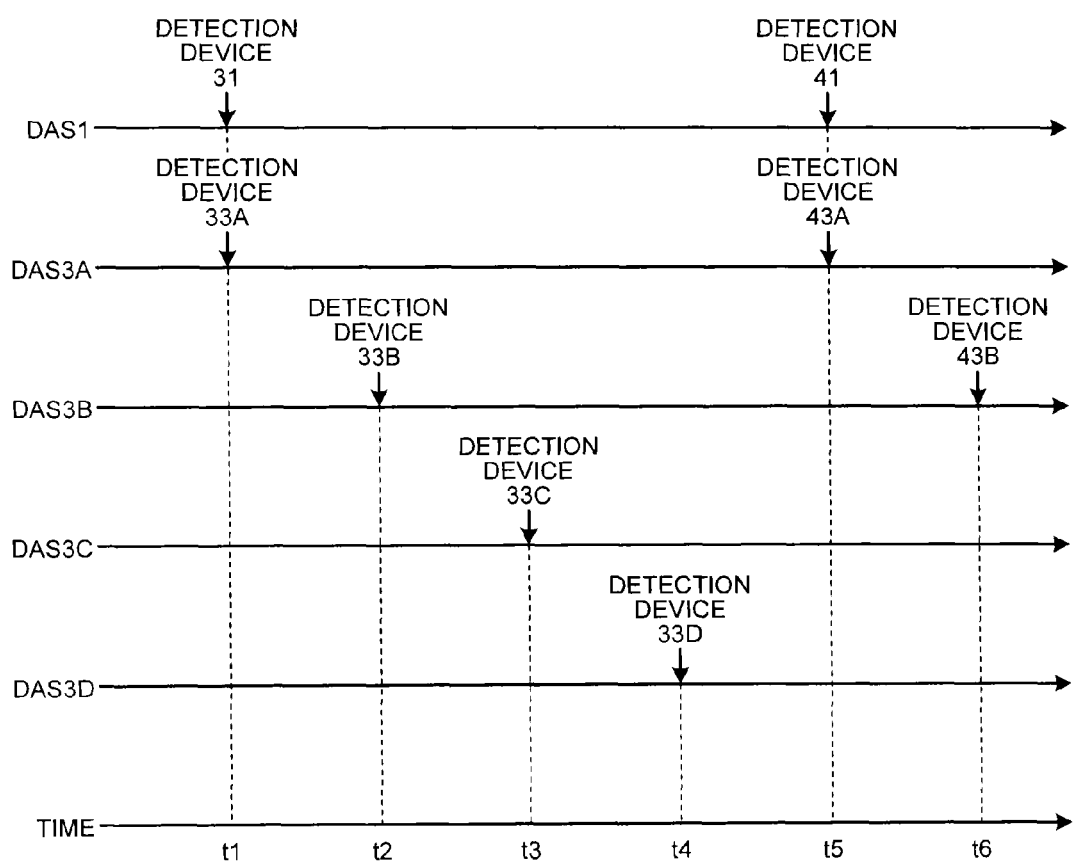
FIG. 8 is a diagram for explaining processing performed by a read control unit according to a third embodiment.

FIG. 8 is a diagram for explaining processing performed by the read control unit 200 according to the third embodiment. In FIG. 8, the horizontal direction corresponds to time. Furthermore, a downward arrow indicates timing of reading a signal by each DAS. In FIG. 8, a case in which signals up to the second column in the slice direction have been read, and signals from the third column are to be read is explained. Moreover, although timing of reading a signal by the DAS 1 and the DASs 3A, 3B, 3C, and 3D exemplified in FIG. 6 is explained herein as one example, the same applies to the other DASs included in the data collecting circuit 116.

In the example indicated in FIG. 8, when read from a detection device having the width of X mm and a detection device group present at the same slice position is synchronized, the read control unit 200 performs control of varying timing of reading from detection devices having the width of Y mm included in the detection device group. In this case, the number of the detection devices having the width of Y mm included in each detection device group is four. Therefore, the read control unit 200 performs control of reducing reading frequency of each DAS to one fourth to vary timing of reading the four detection devices. Specifically, at time t1, the read control unit 200 causes the DAS 1 to perform read from the detection device 31, and causes the DAS 3A to perform read from the detection device 33A. Subsequently, at time t2, the read control unit 200 causes the DAS 3B to perform read from the detection device 33B. Furthermore, at time t3, the read control unit 200 causes the DAS 3C to perform read from the detection device 33C. At time t4, the read control unit 200 causes the DAS 3D to perform read from the detection device 33D. At time t5, the read control unit 200 causes the DAS 1 to perform read from the detection device 41, and causes the DAS 3A to perform read from the detection device 43A. Moreover, at time t6, the read control unit 200 causes the DAS 3B to perform read from the detection device 43B.

As described, the read control unit 200 synchronizes read from the detection device having the width of X mm and the detection device group that are present at the same slice position.

In other words, when the second detection devices included in a detection device group are read by respective different reading units, the read control unit 200 performs control of varying timing of reading each of the second detection devices included in the detection device group, as adjustment control.

Although a case in which the DAS 3 reads the detection devices in the sequence of 33A, 33B, 33C, and 33D at read of the detection device group 33 has been explained in FIG. 8, it is not limited thereto. For example, the DAS 3 may read the detection devices in the sequence of 33A, 33C, 33B, and 33D, or in another sequence. Moreover, time at which the DAS 1 reads the detection device 31 is not limited to time t1, and for example, it may be either one of times t2 to t4. That is, the timing at which the detection device 31 is read is only required to be synchronized with timing at which at least one of the detection devices included in the detection device group at the same slice position.

As described above, the X-ray CT apparatus 100 according to the first embodiment includes a hybrid detector that has two detection regions spatial resolutions of which differ from each other. Furthermore, the X-ray CT apparatus 100 has a DAS for each of detection devices included in each detection device group. The X-ray CT apparatus 100 reads detection devices included in a detection device group at respective different timing. Therefore, the X-ray CT apparatus 100 can suppress occurrence of cross talk.

Fourth Embodiment

In the first embodiment and the third embodiment, a case in which read of a detection device having the width of X mm and a detection device group present at the same slice position is synchronized within a certain range (for example, t1 to t4) has been explained. In this case, the exposure time (period) during which each detection device is exposed by X-rays varies in a strict sense.

Figure 9:
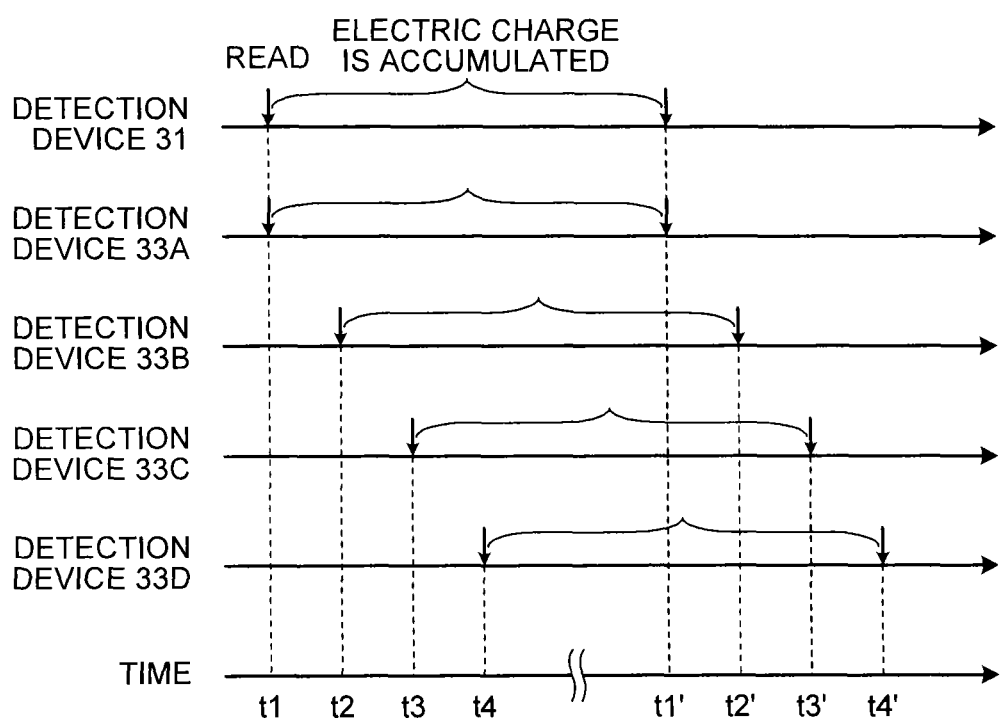
FIG. 9 is a diagram for explaining relation between read of a signal from a detection device and exposure period.

FIG. 9 is a diagram for explaining relation between read of a signal from a detection device and exposure period. In FIG. 9, the horizontal direction corresponds to time. Moreover, a downward arrow indicates timing of read of a signal (electric charge). Moreover, although timing of the detection devices 31, 33A, 33B, 33C, and 33D are exemplified in FIG. 9 as one example, the same applies to the other detection devices included in the X-ray detector 115. Furthermore, although a case in which the DAS 3 performs read of signals from the detection devices 33A, 33B, 33C, and 33D (corresponding to the first embodiment) is explained herein, the following explanation is also similarly applicable to a case in which the DAS 3A, 3B, 3C, and 3D independently performs read of signals from the detection devices 33A, 33B, 33C, and 33D (corresponding to the third embodiment).

As indicated FIG. 9, at time t1, read of the detection device 31 and the detection device 33A is performed. Subsequently, at time t2, read of the detection device 33B is performed. Then, at time t3, read of the detection device 33C is performed. Then, at time t4, read of the detection device 33D is performed. Thereafter, the other detection devices included in the X-ray detector 115 are also read sequentially.

When read from all of the detection devices for X-rays irradiated at one angle are completed, read for a next angle is started. That is, read of the detection device 31 and the detection device 33A is performed at time t1'. Subsequently, at time t2', read of the detection device 33B is performed. Then at time t3', read of the detection device 33C is performed. Then, at time t4', read of the detection device 33D is performed. Thereafter, the other detection devices included in the X-ray detector 115 are also read sequentially in a similar manner.

A signal read at time t1' corresponds to an electric charge accumulated by exposure from time t1 to time t1', for example. Moreover, a signal read at time t2' corresponds to an electric charge accumulated by exposure from time t2 to time t2'. Furthermore, a signal read at time t3' corresponds to an electric charge accumulated by exposure from time t3 to time t3'. Moreover, a signal read at time t4' corresponds to an electric charge accumulated by exposure from time t4 to time t4'.

Thus, signals read from the detection devices 31, 33A, 33B, 33C, and 33D correspond to exposure during a different period in a strict sense. Therefore, it is preferable that raw data output from each of the detection devices be corrected using the amount of X-rays at the time of application of X-rays to each of the detection devices. Accordingly, in the fourth embodiment, a case in which the X-ray CT apparatus 100 corrects raw data that is output from each detection device using the amount of X-rays when X-rays are applied to each detection device.

Figure 10:
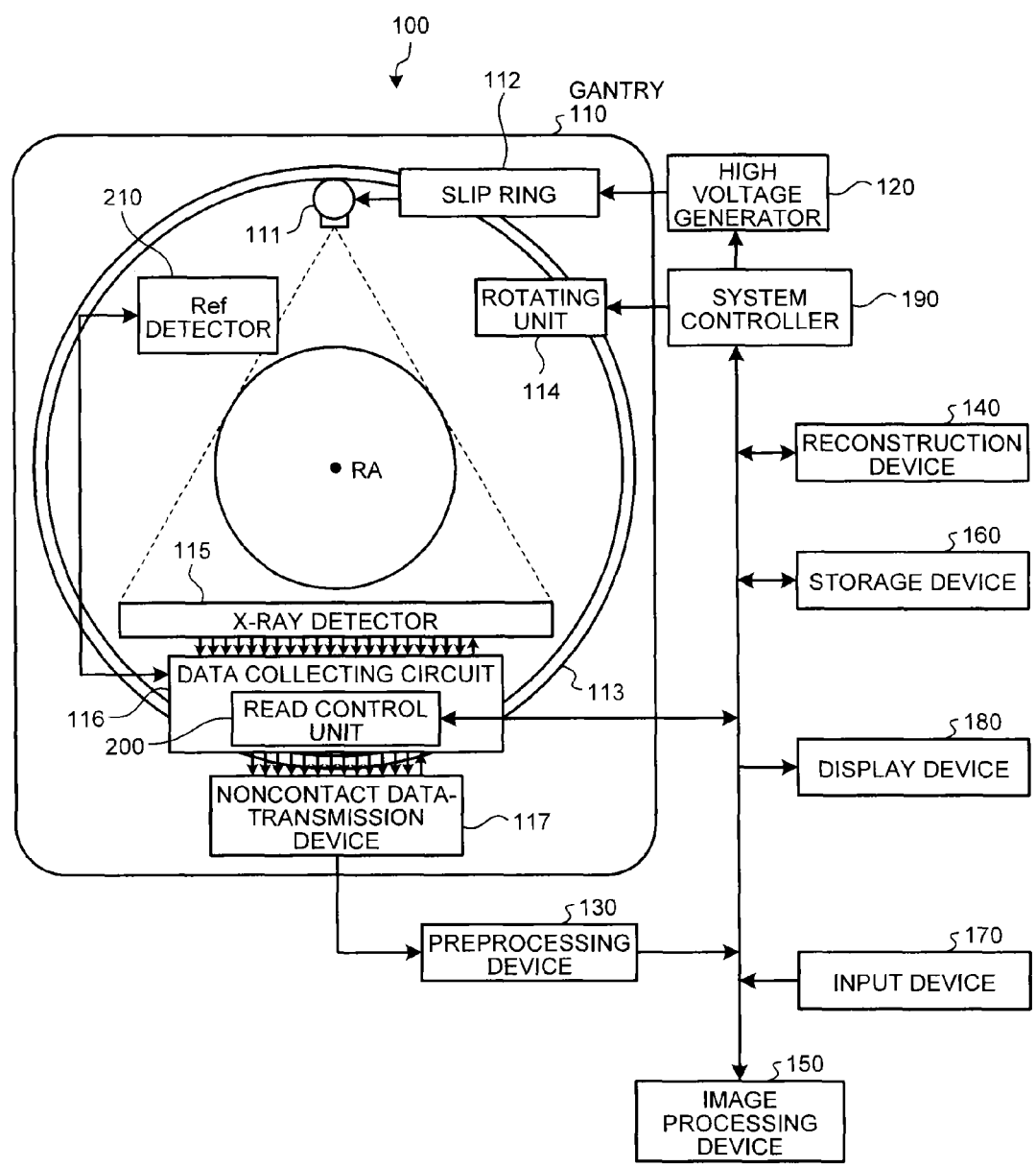
FIG. 10 is a configuration diagram of an X-ray CT apparatus according to a fourth embodiment.

FIG. 10 is a configuration diagram of the X-ray CT apparatus 100 according to the fourth embodiment. The X-ray CT apparatus 100 according to the fourth embodiment has a configuration similar to that of the X-ray CT apparatus 100 indicated in FIG. 1, but has differences in that a Ref (reference) detector 210 is arranged in proximity to the X-ray tube 111, and in a part of processing performed by the data collecting circuit 116 and the preprocessing device 130. Therefore, in the fourth embodiment, points that differ from the first embodiment are mainly explained, and explanation of points with functions similar to the configuration that has been explained in the first embodiment is omitted.

The Ref detector 210 according to the fourth embodiment includes a detection device. The detection device of the Ref detector 210 detects a signal (X-ray non-transmission signal) of X-rays not passing through a subject. The detection device of the Ref detector 210 sequentially outputs detected X-ray non-transmission signals to the data collecting circuit 116. It is desirable that this detection device be formed with the same material as the detection devices 11 to 42.

The data collecting circuit 116 according to the fourth embodiment has a function similar to the function explained in the first embodiment. The data collecting circuit 116 further includes a DAS (Ref DAS) to process an X-ray non-transmission signal detected by the Ref detector 210.

The Ref DAS generates data (reference data) corresponding to exposure time of each detection device in the X-ray detector 115 based on the X-ray non-transmission signal detected by the Ref detector 210, under control by the read control unit 200.

FIG. 11 is a diagram for explaining generation of reference data according to the fourth embodiment. In FIG. 11, the horizontal direction corresponds to time. Moreover, a downward arrow indicates timing of reading a signal (electric charge). Moreover, although the detection devices 31, 33A, 33B, 33C, and 33D are exemplified in FIG. 11 as one example, the same applies to the other detection devices included in the X-ray detector 115. Furthermore, although a case in which the DAS 3 performs read of signals from the detection devices 33A, 33B, 33C, and 33D (corresponding to the first embodiment) is explained herein, the following explanation is also similarly applicable to a case in which the DAS 3A, 3B, 3C, and 3D independently performs read of signals from the detection devices 33A, 33B, 33C, and 33D (corresponding to the third embodiment).

As indicated in FIG. 11, the Ref DAS generates reference data A, B, C, and D for respective raw data output from the detection devices 31, 33A, 33B, 33C, and 33D.

Specifically, the Ref DAS has a capacitor and accumulate the X-ray non-transmission signal (electric charge) that is output from the Ref detector 210. The Ref DAS then reads signals accumulated in the capacitor at timing of reading each of the detection devices 31, 33A, 33B, 33C, and 33D. In the example in FIG. 11, the Ref DAS reads signals at times t1, t2, t3, t4, t1', t2', t3', and t4'. The signals read in this process correspond to electric charges accumulated by non-transmission X-rays in respective periods of t1 to t2, t2, to t3, ..., t3' to t4'. The Ref DAS then amplifies the signals read in each of the periods, and further converts into data (period data) of a digital signal. This period data corresponds to a moving average of signals of each of the periods.

The Ref DAS then generates reference data corresponding to a period in which each of the detection devices 31, 33A, 33B, 33C, and 33D is exposed as indicated in FIG. 11. Specifically, the Ref DAS generate reference data of each detection device by adding respective period data. For example, the Ref DAS generates reference data A by adding period data corresponding to the period of t1 to t1' for the detection device 31 and the detection device 33A. That is, the Ref DAS generates reference data A by adding the period data of the respective periods t1 to t2, t2 to t3, ..., to t1'. Moreover, the Ref DAS generates reference data B by adding period data corresponding to the period of t2 to t2' for the detection device 33B. Furthermore, the Ref DAS generates reference data C by adding period data corresponding to the period of t3 to t3' for the detection device 33C. Moreover, the Ref DAS generates reference data D by adding period data corresponding to the period of t4 to t4' for the detection device 33D.

The data collecting circuit 116 adds the reference data corresponding to each raw data to raw data that is derived from each of the detection devices 31, 33A, 33B, 33C, and 33D. For example, the data collecting circuit 116 adds reference data A to raw data that is derived from the detection device 31. Moreover, the data collecting circuit 116 adds reference data A to raw data that is derived from the detection device 33A. Furthermore, the data collecting circuit 116 adds reference data B to raw data that is derived from the detection device 33B. Moreover, the data collecting circuit 116 adds reference data C to raw data that is derived from the detection device 33C. Furthermore, the data collecting circuit 116 adds reference data D to raw data that is derived from the detection device 33D.

The preprocessing device 130 according to the fourth embodiment performs correction processing to correct each raw data using reference data added to each raw data. For example, an output ratio (=raw data/reference data) is acquired. This output ratio indicates attenuation of X-rays by a subject.

For example, the preprocessing device 130 divides raw data derived from the detection device 31 by reference data A. Moreover, the preprocessing device 130 divides raw data derived from the detection device 33A by reference data A. Furthermore, the preprocessing device 130 divides raw data derived from the detection device 33B by reference data B. Moreover, the preprocessing device 130 divides raw data derived from the detection device 33C by reference data C. Furthermore, the preprocessing device 130 divides raw data derived from the detection device 33D by reference data D.

As described, the X-ray CT apparatus 100 according to the fourth embodiment enables correction of raw data that is output from each detection device using the amount of X-rays at the time of application of X-rays to each detection device.

According to at least one of the embodiments explained above, the image quality of a generate image can be improved.

According to the X-ray CT apparatus of the embodiments, it is possible to improve the image quality of a generated image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computer-tomography (CT) apparatus, comprising:
an X-ray tube that rotates about a body axis of a subject, and that generates X-rays;
an X-ray detector that has a first detection region and a second detection region, at least a part of the second detection region being aligned with the first detection region along a channel direction, the first detection region having a plurality of first detection devices, which detect X-rays passing through the subject, arranged in a slice direction and the channel direction, the second detection region having a plurality of second detection devices, each having a width smaller in the slice direction than that of the first detection device, arranged in the slice direction and the channel direction;
a reading circuit that reads a signal of the X-rays that are detected by at least one of the first detection device and the second detection device; and
a read control circuit that adjusts timing of reading signals from a certain first detection device and a certain second detection device according to a difference between a size of the certain first detection device and a size of the certain second detection device in such a manner that a time difference in reading of the signals from the certain first detection device and the certain second detection device that are present at positions corresponding to each other in the slice direction decreases.

2. The X-ray CT apparatus according to claim 1, wherein when reading a detection device group that detects the X-rays in a range identical in size to the certain first detection device and in which at least two of the second detection devices are arranged in each of the slice direction and the channel direction, the read control circuit synchronizes timing of reading the certain first detection device and at least one timing of reading the respective second detection devices that are included in the detection device group present at a position corresponding to the certain first detection device in the slice direction.

3. The X-ray CT apparatus according to claim 2, wherein when the second detection devices included in the detection device group are read by a same reading circuit, the read control circuit reduces a frequency of reading the certain first detection device according to a number of the second detection devices included in the detection device group.

4. The X-ray CT apparatus according to claim 3, further comprising:
a non-transmission-X-ray detector that detects X-rays generated from the X-ray tube, and not passing through the subject;
a non-transmission-signal reading circuit that reads a non-transmission signal according to a timing of reading by the read control circuit at each timing, the non-transmission signal being a signal corresponding to X-rays that are detected by the non-transmission-X-ray detector; and
an image generator that corrects the signal of the X-rays read by the reading circuit by using the non-transmission signal at each of the timing read by the non-transmission-signal reading circuit, to generate an image.

5. The X-ray CT apparatus according to claim 2, wherein when the second detection devices included in the detection device group are read by respective different reading circuits, the read control circuit synchronizes a timing of reading the certain first detection device that is present at a position corresponding to the detection device group in the slice direction, and a timing of reading respective devices of the second detection devices.

6. The X-ray CT apparatus according to claim 2, wherein when the second detection devices included in the detection device group are read by respective different reading circuits, the read control circuit performs control to vary timing of reading respective devices of the second detection devices included in the detection device group.

7. The X-ray CT apparatus according to claim 6, further comprising:
a non-transmission-X-ray detector that detects X-rays generated from the X-ray tube, and not passing through the subject;
a non-transmission-signal reading circuit that reads a non-transmission signal according to a timing of reading by the read control circuit at each timing, the non-transmission signal being a signal corresponding to X-rays that are detected by the non-transmission-X-ray detector; and
an image generator that corrects the signal of the X-rays read by the reading circuit by using the non-transmission signal at each timing read by the non-transmission-signal reading circuit, to generate an image.

8. The X-ray CT apparatus according to claim 2, further comprising:
a non-transmission-X-ray detector that detects X-rays generated from the X-ray tube, and not passing through the subject;
a non-transmission-signal reading circuit that reads a non-transmission signal according to a timing of reading by the read control circuit at each timing, the non-transmission signal being a signal corresponding to X-rays that are detected by the non-transmission-X-ray detector; and
an image generator that corrects the signal of the X-rays read by the reading circuit by using the non-transmission signal at each timing read by the non-transmission-signal reading circuit, to generate an image.

* * * * *